United States Patent
Evenou et al.

(10) Patent No.: US 7,358,253 B2
(45) Date of Patent: *Apr. 15, 2008

(54) INDOLYLMALEIMIDE DERIVATIVES

(75) Inventors: Jean-Pierre Evenou, St. Louis (FR); Peter Von Matt, Biel-Benken (CH); Jürgen Wagner, Bottmingen (CH); Gerhard Zenke, Rheinfelden (DE)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/546,690

(22) Filed: Oct. 12, 2006

(65) Prior Publication Data

US 2007/0032507 A1 Feb. 8, 2007

Related U.S. Application Data

(63) Continuation of application No. 10/510,027, filed as application No. PCT/EP03/03470 on Apr. 2, 2003, now abandoned.

(30) Foreign Application Priority Data

Apr. 3, 2002 (GB) .................................. 0207729.5
Feb. 13, 2003 (GB) .................................. 0303323.0

(51) Int. Cl.
*A61K 31/496* (2006.01)
(52) U.S. Cl. .................... 514/252.19; 514/252.13; 514/253.04; 514/254.09; 514/254.01
(58) Field of Classification Search ................ 544/295, 544/363; 514/252.1
See application file for complete search history.

(56) References Cited

U.S. PATENT DOCUMENTS

| 6,645,970 | B2 | 11/2003 | Albert et al. | ............ 514/266.2 |
| 2007/0037826 | A1* | 2/2007 | Evenou et al. | ......... 514/252.19 |

FOREIGN PATENT DOCUMENTS

| EP | 0 328 026 | 8/1989 |
| EP | 1 120 414 | 8/2001 |
| WO | 01/46178 | 6/2001 |
| WO | 02/10158 | 2/2002 |
| WO | 02/38561 | 5/2002 |

* cited by examiner

Primary Examiner—Kamal A. Saeed
Assistant Examiner—Michael P. Barker
(74) Attorney, Agent, or Firm—Leslie Fischer; Thomas R. Savitsky

(57) ABSTRACT

Provided are compounds of formula (I)

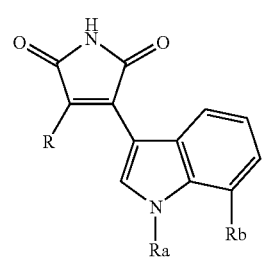

which are useful in the treatment and/or prevention of diseases or disorders mediated by T lymphocytes and/or PKC, e.g. acute or chronic rejection of organ or tissue allo- or xenografts, graft versus host diseases, atherosclerosis, vascular occlusion due to vascular injury such as angioplasty, restenosis, obesity, syndrome X, impaired glucose tolerance, polycystic ovary syndrome, hypertension, heart failure, chronic obstructive pulmonary disease, CNS diseases such as Alzheimer disease or amyotrophic lateral sclerosis, cancer, infectious diseases such as AIDS, septic shock or adult respiratory distress syndrome, ischemia/reperfusion injury e.g. myocardial infarction, stroke, gut ischemia, renal failure or hemorrhage shock, or traumatic shock, e.g. traumatic brain injury. The compounds of formula I are also useful in the treatment and/or prevention of T-cell mediated acute or chronic inflammatory disease or disorders or autoimmune diseases e.g. rheumatoid arthritis, osteoarthritis, systemic lupus erythematosus, Hashimotos thyroidis, multiple sclerosis, myasthenia gravis, diabetes type I or II and the disorders associated therewith, e.g. angiopathy, diabetic proliferative retinopathy, diabetic macular edema, nephropathy, neuropathy and dawn phenomenon, respiratory diseases such as asthma or inflammatory lung injury, inflammatory liver injury, inflammatory glomerular injury, cutaneous manifestations of immunologically-mediated disorders or illnesses, inflammatory and hyperproliferative skin diseases (such as psoriasis, atopic dermatitis, allergic contract dermatitis, irritant contact dermatitis and further eczematous dermatitises, seborrhoeic dermatitis), inflammatory eye diseases, e.g. Sjoegren's syndrome, keratoconjunctivitis or uveitis, inflammatory bowel disease, Crohn's disease or ulcerative colitis.

4 Claims, No Drawings

INDOLYLMALEIMIDE DERIVATIVES

This is a continuation of application Ser. No. 10/510,027 filed on Oct. 1, 2004, which is 371 of Application No. PCT/EP03/03470 filed on Apr. 2, 2003, the entire disclosures of which are hereby incorporated by reference.

The present invention relates to indolylmaleimide derivatives, process for their production and pharmaceutical compositions containing them.

More particularly the present invention provides a compound of formula I

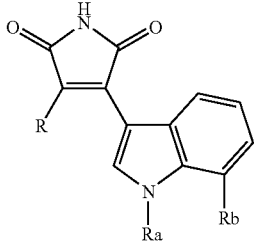

wherein
$R_a$ is H; $CH_3$; $CH_2$—$CH_3$; or isopropyl,
$R_b$ is H; halogen; $C_{1-6}$alkoxy; or $C_{1-6}$alkyl, and either
I. R is a radical of formula (a)

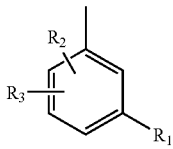

wherein
$R_1$ is piperazin-1-yl optionally substituted by $CH_3$ in position 3 or 4; or 4,7-diaza-spiro [2.5] oct-7-yl;
$R_2$ is Cl; Br; $CF_3$; or $CH_3$; and
$R_3$ is H; $CH_3$; or $CF_3$; $R_2$ being other than $CH_3$ or Cl when $R_3$ is H, $R_a$ is H or $CH_3$, $R_b$ is
H and $R_1$ is 4-methyl-1-piperazinyl; or
II. R is a radical of formula (b)

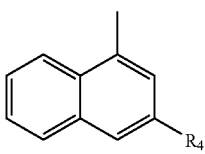

wherein
$R_4$ is 1-piperazinyl substituted in positions 3 and/or 4 by $CH_3$; or 4,7-diaza-spiro [2.5] oct-7-yl; $R_a$ being other than H or $CH_3$ when R is 4-methyl-1-piperazinyl; or III. R is a residue of formula (c)

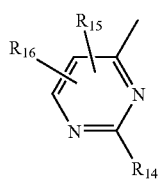

wherein
$R_{14}$ is 1-piperazinyl optionally substituted by $CH_3$ in position 3 and/or 4 or in position 3 by ethyl, phenyl-$C_{1-4}$alkyl, $C_{1-4}$alkoxy-$C_{1-4}$alkyl or halogeno-$C_{1-4}$alkyl; or
4,7-diaza-spiro [2.5] oct-7-yl;
$R_{15}$ is halogen; $CF_3$; or $CH_3$; $R_{15}$ being other than $CH_3$ when $R_{16}$ is $CH_3$, $R_a$ is H or
$CH_3$, $R_b$ is H and $R_{1-4}$ is 4-methyl-1-piperazinyl; and
$R_{16}$ is H; $CH_3$; $CH_2$—$CH_3$; or $CF_3$; $R_{16}$ being other than H when $R_{15}$ is Cl, $R_a$ is H or
$CH_3$, $R_b$ is H and $R_{14}$ is 4-methyl-1-piperazinyl; or
IV. R is a radical of formula (d)

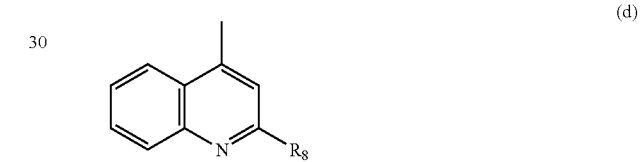

wherein $R_8$ is 1-piperazinyl, 3-methyl-piperazin-1-yl or 4-benzyl-piperazin-1-yl; or
V. R is a radical of formula (e)

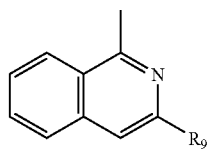

wherein $R_9$ is 4,7-diaza-spiro [2.5] oct-7-yl; or piperazin-1-yl substituted in position 3 by methyl or ethyl and optionally in position 4 by methyl.

The compounds of formula I may exist in free form or in salt form, e.g. addition salts with e.g. organic or inorganic acids, for example, hydrochloric acid, acetic acid, trifluoroacetic acid.

It will be appreciated that the compounds of formula I may exist in the form of optical isomers, racemates or diastereoisomers. For example, a ring carbon atom bearing a substituent in the position 3 of the piperazinyl residue is asymmetric and may have the R— or S-configuration. It is to be understood that the present invention embraces all enantiomers and their mixtures. Enantiomers are preferred over racemates. Similar considerations apply in relation to starting materials exhibiting asymmetric carbon atoms as mentioned.

Alkyl or alkoxy may be straight or branched. Phenyl-$C_{1-4}$alkyl is preferably benzyl or phenethyl. In $C_{1-4}$alkoxy-$C_{1-4}$alkyl the alkoxy moiety is preferably methoxy or ethoxy and the alkyl moiety preferably methyl or ethyl; a suitable example is e.g. 2-methoxyethyl. Halogen may be F, Cl, Br or I, preferably F, Cl or Br. Halogeno-$C_{1-4}$alkyl is alkyl wherein one or more H are replaced by halogen, e.g. Cl or F, e.g. $CH_2Cl$, $CH_2F$ or $CF_3$ R is preferably a radical of formula (a), (c) or (e), preferably (e).

In the radical of formula (a) or (c), $R_2$ or $R_{15}$ is preferably in para to $R_1$ or $R_{14}$, respectively. $R_3$ is preferably in meta to $R_1$. In the radical or formula (e), $R_9$ is preferably 4,7-diazaspiro [2.5] oct-7-yl; when $R_9$ is piperazinyl substituted in position 3, it has the R or S configuration.

The present invention also includes a process for the preparation of a compound of formula I which process comprises reacting a compound of formula II

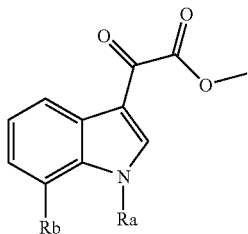

(II)

wherein $R_a$ and $R_b$ are as defined above,
with a compound of formula III

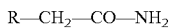

R—$CH_2$—CO—$NH_2$ (III)

wherein R is as defined above, and, where required, converting the resulting compound of formula I obtained in free form to a salt form or vice versa, as appropriate.

The process may conveniently be effected in the presence of a strong base, e.g. t-BuOK, e.g. as disclosed in WO02/38561, the contents of which being incorporated herein by reference, and as illustrated in the Examples.

Compounds of formula II and III may be prepared in accordance with known methods, e.g. as disclosed in WO02/38561, the contents of which being incorporated herein by reference, and as illustrated in the Examples.

Insofar as the production of the starting materials is not particularly described, the compounds are known or may be prepared analogously to methods known in the art or as described hereafter.

The following examples are illustrative of the invention without any limitation.
RT=room temperature
THF=tetrahydrofuran
FCC=flash column chromatography
TBAF=tetrabutyl ammonium fluoride
BINAP=2,2'-bis(diphenylphosphino)-1,1'-binaphthyl
$Pd_2(dba)_3$=Pd(0)-bis(dibenzylideneacetone)

EXAMPLE 1

3-[2-Chloro-3-methyl-6(4-methyl-piperazin-1-yl)-phenyl]-4-(1H-indol-3-yl)-pyrrole-2,5dione

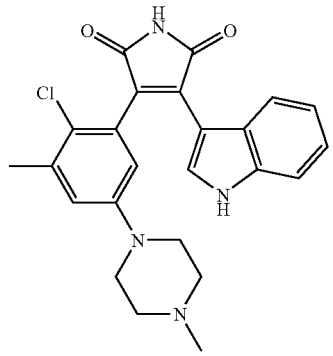

2-[2-Chloro-3-methyl-5-(4-methyl-piperazin-1-yl)-phenyl]-acetamide (211 mg, 0.75 mmol) and 3-indoleglyoxylate (270 mg, 1.35 mmol) are dissolved in THF (5 mL). A solution of 1.0 M tert-BuOK in THF (2.98 mL, 4 eq) is added and the mixture is stirred at 35° C. overnight. The reaction is diluted with AcOEt (20 mL) and washed with $H_2O$ (20 mL) and brine (10 mL). The organic phase is dried over $Na_2SO_4$ and the solvent is evaporated. The residue is purified by FCC (AcOEt/AcOH/$H_2O$ 7:1:1) to afford the title compound in the form of its acetate salt.

$^1$H NMR (DMSO, 400 MHz) δ 2.16 (s, 3H), 2.31 (s, 3H), 2.32-2.38 (m, 4H), 2.97-3.10 (m, 4H), 6.61 (d, J=8.0 Hz, 1H), 6.71-6.77 (m, 2H), 7.04 (d, J=2.8 Hz, 1H), 7.08 (dd, J=7.4, 7.2 Hz, 1H), 7.41 (d, J=8.2 Hz, 1H), 7.98 (d, J=1.5 Hz, 1H), 11.05 (br s, 1H), 11.90 (br s, 1H); ES-MS: 435 [M+H]$^+$.

2-[2-Chloro-3-methyl-5-(4-methyl-piperazin-1-yl)-phenyl]-acetamide

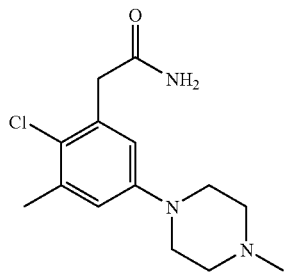

used as starting material may be prepared as follows:
(5Bromo-2-chloro-3-methyl-phenyl)-acetic acid methyl ester (2.0 g, 7.2 mmol), N-methylpiperazine (960 μL, 8.6 mmol) and $Cs_2CO_3$ (3.3 g, 10.1 mmol) are suspended in toluene (80 mL). Pd(OAc)$_2$ (81 mg, 0.36 mmol) and BINAP (224 mg, 0.36 mmol) are added and the reaction is stirred at 100° C. overnight. The mixture is filtered through Celite and the solvent is evaporated. The residue is purified by FCC (AcOEt/AcOH/$H_2O$ 60:15:15) to afford 2-[2-chloro-3-methyl-5(4-methyl-piperazin-1-yl)-phenyl]-acetic acid methyl ester. The ester is suspended in $NH_4OH$ 25% (60 mL). The mixture is stirred overnight at RT and the precipitate is filtered off to yield the amide. $^1$H NMR (DMSO, 400 MHz)

δ 2.20 (s, 3H), 2.27 (s, 3H), 2.40-2.45 (m, 4H), 3.07-3.13 (m, 4H), 3.48 (s, 2H), 6.78 (s, 1H), 6.82 (s, 1H), 6.91 (br s, 1H), 7.34 (br s, 1H).

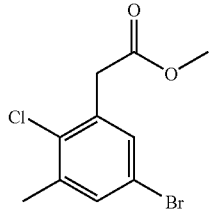

CuCl$_2$ (8.0 g, 0.06 mol) and tert-butylnitrile (8.9 mL, 0.074 mol) are suspended in acetonitrile (60 mL). 1,1-dichloroethylene is added dropwise at 20° C. 5-Bromo2-chloro-3-methyl-phenylamine (11.0 g, 0.05 mol), dissolved in acetonitrile (60 mL), is added and the reaction is stirred at RT for 3 h. The mixture is poured into aqueous 20% HCl (150 mL) and the aqueous phase is extracted with CH$_2$Cl$_2$ (2×150 mL). The organic phase is dried over Na$_2$SO$_4$ and the solvent is evaporated. The residue is purified by FCC (hexane/CH$_2$Cl$_2$ 9:1) to afford 5-bromo-2-chloro-1-methyl-3-(2,2,2-trichloro-ethyl)-benzene. The intermediate is redissolved in MeOH (80 mL) and heated to 70° C. A solution of 5.4 M NaOMe in MeOH (28.4 mL) is added dropwise and the reaction is stirred at 70° C. for 3 h. The reaction is cooled to RT and concentrated H$_2$SO$_4$ (10 mL) is added. The reaction is stirred at reflux for 1 h. The mixture is diluted with H$_2$O (200 mL) and extracted with CH$_2$Cl$_2$ (2×200 mL). The combined organic phases are dried over Na$_2$SO$_4$ and the solvent is evaporated. The residue is purified by FCC (hexane/CH$_2$Cl$_2$ 9:1 to 1:1) to afford (5bromo-2-chloro-3-methyl-phenyl)-acetic acid methyl ester. $^1$H NMR (CDCl$_3$, 400 MHz) δ 2.26 (s, 3H), 3.61 (s, 3H), 3.63 (s, 2H), 7.15 (s, 1H), 7.21 (s, 1H).

By following the procedure of Example 1 but using the appropriate starting materials, the compounds of formula I wherein R is a residue of formula (a), as indicated in Table 1 below may be obtained.

EXAMPLE 20

3-[3-(4,7-Diaza-spiro[2.5] oct-7-yl)-naphthalen-1-yl]-4-(1-methyl-1H-indol-3-yl)-pyrrole-2,5-dione

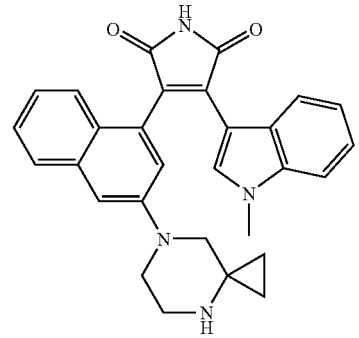

2-[3-(4,7-Diaza-spiro[2.5] oct-7-yl)-naphthalen-1-yl]-acetamide (100 mg, 0.30 mmol) and (1-methyl-1H-indol-3-yl)-oxo-acetic acid methyl ester (97 mg, 0.44 mmol) are azeotroped three times with dry THF and then dissolved in dry THF (3 ml). A solution of 1.0 M KOtBu in THF (1.2 ml) is added dropwise over 20 minutes at RT. After 5 minutes, TLC analysis indicates complete conversion of starting materials. The reaction is quenched by the additon of water (5 ml). The mixture is diluted with EtOAc and washed twice with saturated aq. NH$_4$Cl. The aqueous layers are back extracted twice with EtOAc. The combined organic layers are dried over Na$_2$SO$_4$ and the solvent is evaporated. The residue is purified by FCC (EtOAc/AcOH/H$_2$O 800:55:45) to afford the title compound as its acetate salt. The compound is dissolved in MeOH/TFA and the solvent is removed to yield the title compound as its trifluoroacetate salt. $^1$H NMR (DMSO, 400 MHz) δ 0.95 (M, 4H), 3.39 (br, 4H), 3.49 (br, 2H), 3.86 (s, 3H), 6.16 (d, J=7.9 Hz, 1H), 6.46 (dd, J=6.6/7.9 Hz, 1H), 7.00 (dd, J=6.6/7.9 Hz, 1H), 7.13 (dd, J=7.6/7.6 Hz, 1H), 7.40 (m, 4H), 7.55 (d, J=8.5 Hz, 1H), 7.78 (d, J=7.6 Hz, 1H), 8.14 (s, 1H), 9.10 (br, 2H), 11.17 (s, 1H); ES-MS: 463 [M+H]$^+$.

TABLE 1

| Example | R$_1$ | R$_2$ | R$_3$ | R$_a$ | R$_b$ | M.S. Data |
|---|---|---|---|---|---|---|
| 2 | -(4-methyl-piperazin-1-yl) | 2-CH$_3$ | 3-CH$_3$ | CH$_3$ | H | MH$^+$ 429 |
| 3 | -(4-methyl-piperazin-1-yl) | 2-CH$_3$ | 3-CH$_3$ | H | H | MH$^+$ 415 |
| 4 | -(4-methyl-piperazin-1-yl) | 2-Cl | 3-CH$_3$ | CH$_3$ | H | MH$^+$ 449 |
| 5 | 1-piperazinyl | 2-Cl | 3-CH$_3$ | H | H | MH$^+$ 421 |
| 6 | 1-piperazinyl | 2-Cl | 3-CH$_3$ | CH$_3$ | H | MH$^+$ 435 |
| 7 | 3-R-methyl-piperazin-1-yl | 2-Cl | 3-CH$_3$ | CH$_3$ | H | MH$^+$ 449 |
| 8 | 3-R-methyl-piperazin-1-yl | 2-Cl | 3-CH$_3$ | H | H | MH$^+$ 435 |
| 9 | 1-piperazinyl | 2-Cl | 3-CF$_3$ | CH$_3$ | H | MH$^+$ 503 |
| 10 | 1-piperazinyl | 2-Cl | 3-CF$_3$ | H | H | MH$^+$ 489 |
| 11 | -(4-methyl-piperazin-1-yl) | 2-Cl | 3-CH$_3$ | H | CH(CH$_3$)$_2$ | MH$^+$ 477 |
| 12 | -(4-methyl-piperazin-1-yl) | 2-Cl | 3-CH$_3$ | H | CH$_3$ | MH$^+$ 449 |
| 13 | -(4-methyl-piperazin-1-yl) | 2-Cl | 3-CH$_3$ | H | CH$_2$—CH$_3$ | MH$^+$ 463 |
| 14 | -(4-methyl-piperazin-1-yl) | 2-Cl | 3-CH$_3$ | H | Cl | MH$^+$ 469 |
| 15 | -(4-methyl-piperazin-1-yl) | 2-Cl | 3-CH$_3$ | H | F | MH$^+$ 453 |
| 16 | -(4,7-diaza-spiro[2.5]oct-7-yl) | 2-Cl | H | H | CH$_2$—CH$_3$ | MH$^+$ 462 |
| 17 | -(4,7-diaza-spiro[2.5]oct-7-yl) | 2-Cl | H | H | Cl | MH$^+$ 468 |
| 18 | -(4,7-diaza-spiro[2.5]oct-7-yl) | 2-Cl | H | H | CH$_3$ | MH$^+$ 447 |
| 19 | -(4,7-diaza-spiro[2.5]oct-7-yl) | 2-Cl | H | H | H | MH$^+$ 434 |

2-[3-(4,7-diaza-spiro[2.5] oct-7-yl)-naphthalen-1-yl]-acetamide, used as starting material may be prepared as follows:

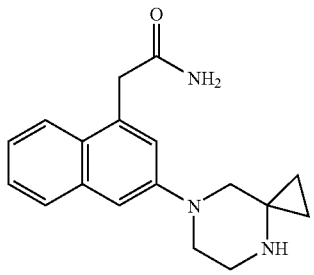

a) 2-[3-(4-Benzyl-4,7-diaza-spiro[2.5] oct-7-yl)-naphthalen-1-yl]-acetamide (280 mg, 0.73 mmol) is azeotroped twice with a 1.25 M solution of HCl in MeOH. The residue is dissolved in EtOH (10 ml). Palladium on charcoal (10%, 77 mg) is added, and the mixture is stirred under an atmosphere of hydrogen (1 atm) at RT for 14 h and at 50° C. for 2 h. The mixture is filtered, and the filtrate is concentrated. The residue is purified by FCC (EtOAc/AcOH/$H_2O$ 750:83.68 to 600:150:150) to yield the title compound containing 0.7 eq of AcOH. $^1$H NMR (DMSO, 400 MHz) δ 0.53 (m, 4H), 1.78 (s, AcOH), 2.93 (ddd, 2H), 3.04 (s, 2H), 3.16 (ddd, 2H), 3.76 (s, 2H), 6.94 (br, 1H), 6.99 (s, 1H), 7.25 (dd, 1H), 7.26 (s, 1H), 7.35 (dd, J=6.7/7.8, 1 H), 7.49 (br, 1H), 7.69 (d, J=7.8, 1H), 7.88 (d, J=10.0, 1H); ES-MS: 296 [M+H]$^+$.

b) 2-[3-(4-Benzyl-4,7-diaza-spiro[2.5] oct-7-yl)-naphthalen-1-yl]-acetamide [3-(4-Benzyl-4,7-diaza-spiro[2.5] oct-7-yl)-naphthalen-1-yl]-acetic acid ethyl ester (347 mg, 0.84 mmol) and formamide (126 mg, 2.80 mmol) are dissolved under an atmosphere of argon in DMF (1 ml). The solution is heated to 105° C., and NaOMe (155 μL of a 5.4 M solution in MeOH, 45 mg, 0.84 mmol) is added dropwise during 15 minutes. After 30 minutes at 105° C., TLC analysis indicates complete consumption of starting material. The reaction mixture is cooled to RT, diluted with water, and extracted with EtOAc. The EtOAc layers are washed twice with water. Removal of solvent and purification by FCC (EtOAc/MeOH 98:2 to 96:4 to 90:10) yielded the title compound. $^1$H NMR (CDCl$_3$, 400 MHz) δ 0.71 (ddd, 2H), 0.89 (ddd, 2H), 3.10 (ddd, 2H), 3.16 (s, 2H), 3.31 (ddd, 2H), 3.93 (s, 2H), 3.99 (s, 2H), 3.99 (s, 2H), 5.33 (br, 1H), 5.42 (br, 1H), 7.11 (s, 1H), 7.23 (d, J=2.0, 1H), 7.32 (m, 5H), 7.37 (dd, J=6.7 Hz, 1H), 7.45 (dd, J=6.7 Hz, 1H), 7.73 (d, J=8.9 Hz, 1H), 7.85 (d, J=8.9 Hz, 1H); ES-MS: 386 [M+H]$^+$.

c) [3-(4-Benzyl-4,7-diaza-spiro[2.5] oct-7-yl)-naphthalen-1-yl]-acetic acid ethyl ester
(3-Trifluoromethanesulfonyloxy-naphthalen-1-yl)-acetic acid ethyl ester (500 mg, 1.38 mmol) is dissolved under an atmosphere of argon in dry THF (10 ml). 4-Benzyl-4,7diaza-spiro[2.5]octane (325 mg, 1.61 mmol) is added, followed by the addition of K$_3$PO$_4$ (410 mg, 1.93 mmol), Pd$_2$(dba)$_3$ (62 mg, 0.069 mmol) and biphenyl-2-yl-di-tert-butyl-phosphane (21 mg, 0.069 mmol). The reaction mixture is heated to 80° C. After 4 h, TLC analysis indicates complete consumption of starting materials. The reaction mixture is cooled to RT, filtered and concentrated. The residue is purified by FCC (hexanes/EtOAc 100:0 to 90;10 to 80:20 to 70:30 to 0:100) to afford the title compound. $^1$H NMR (CDCl$_3$, 400 MHz) δ 0.69 (ddd, 2H), 0.86 (ddd, 2H), 1.24 (t, J=7.0 Hz, 3H), 3.09 (ddd, 2H), 3.19 (s, 2H), 3.31 (ddd, 2H), 3.93 (s, 2H), 4.02 (s, 2H), 4.17 (q, J=7.0 Hz, 2H), 7.08 (s, 1H), 7.21 (s, 1H), 7.33 (m, 6H), 7.42 (dd, J=8.8 Hz, 1H), 7.71 (d, J=8.8 Hz, 1H), 7.88 (d, J=8.8 Hz, 1H); ES-MS: 415 [M+H]$^+$.

d) (3-Trifluoromethanesulfonyloxy-naphthalen-1-yl)-acetic acid ethyl ester

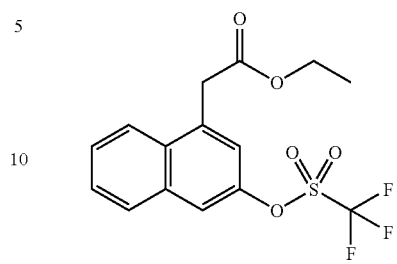

(3-Hydroxy-naphthalen-1-yl)-acetic acid ethyl ester (1.67 g, 7.25 mmol) is dissolved in CH$_2$Cl$_2$ (20 ml) under an atmosphere of argon. Pyridine (1.17 ml, 1.15 g, 14.50 mmol) is added, and the reaction mixture is cooled to 0° C., whereupon trifluoromethanesulfonic anhydride (1.79 ml, 3.07 g, 10.88 mmol) is added dropwise. The reaction mixture is warmed to RT, and after 1 h a RT, TLC analysis indicates complete consumption of starting material. The reaction mixture is diluted with EtOAc and washed twice with H$_2$O. The combined organic layers are dried over Na$_2$SO$_4$, the solvent is removed, and the residue is purified by FCC (hexanes/EtOAc 100:0 to 97:3 to 95:5 to 93:7 to 90:10) to yield the title compound. $^1$H NMR (DMSO, 400 MHz) δ 1.19 (t, J=7.2 Hz, 3H), 4.11 (q, J=7.2 Hz, 2H), 4.38 (s, 2H), 7.60 (d, J=3.0 Hz, 1H), 7.70 (m, 2H), 8.03 (m, 1H), 8.12 (m, 2H); ES-MS: 362 [M+H]$^+$.

e) (3-Hydroxy-naphthalen-1-yl)-acetic acid ethyl ester
(3-Benzyloxy-naphthalen-1-yl)-acetic acid ethyl ester (2.43 g, 7.58 mmol) is dissolved in MeOH (50 ml). Palladium on charcoal (807 mg) is added, and the reaction mixture is stirred at RT under an atmosphere of hydrogen (1 atm) for 14 h. The reaction mixture is filtered. Concentration yields the pure title compound. $^1$H NMR (DMSO, 400 MHz) δ 1.18 (t, J=7.2 Hz, 3H), 4.05 (s, 2H), 4.10 (q, J=7.2 Hz, 2H), 7.04 (d, J=1.8 Hz, 1H), 7.06 (d, J=1.8, 1H), 7.30 (t, J=7.8, 1H), 7.40 (t, J=7.8, 1H), 7.70 (d, J=7.8, 1H), 7.80 (d, J=7.8 Hz, 1H); ES-MS: 230 [M+H]$^+$.

f) (3-Benzyloxy-naphthalen-1-yl)-acetic acid ethyl ester
3-Benzyloxy-1-bromo-naphthalene (5.64 g, 18.01 mmol) is dissolved under an atmosphere of argon in dry DMF (100 ml). Tributylstannanyl-acetic acid ethyl ester (7.47 g, 19.81 mmol) is added, as well as [bis(tri-ortho-tolyl-phosphine)] palladium (II) dichloride (2.83 g, 3.60 mmol) and zinc(II) bromide (5.27 g, 23.41 mmol). The reaction mixture is heated to 80° C. for 3 h. The reaction mixture is diluted with EtOAc and washed twice with diluted brine (back extracted). The combined organic layers are dried over Na$_2$SO$_4$, the solvent is removed, and the residue is purified by FCC (hexane/EtOAc 100:0 to 97.5:2.5 to 95:5 to 90:10). The resulting oil, still containing tin residues, is stirred in a 1:1 mixture of EtOAc/1N NaOH (200 ml) for 1 h. The mixture is extracted twice with EtOAc. The combined organic layers are washed twice with H$_2$O (back extracted), dried over Na$_2$SO$_4$ and concentrated. The residue is purified by FCC (hexane/EtOAc 100:0 to 97:3 to 95:5 to 93:7 to 92:8 to 90:10) to yield the title compound. $^1$H NMR (DMSO, 400 MHz) δ 1.18 (t, J=7.2 Hz, 3H), 4.10 (q, J=7.2 Hz, 2H), 4.11 (s, 2H), 5.25 (s, 2H), 7.21 (d, J=3.0 Hz, 1H), 7.41 (m, 8H), 7.53 (d, J=6.6 Hz, 1H), 7.84 (dd, J=7.2 Hz, 1H); ES-MS: 320 [M+H]$^+$.

g) 3-Benzyloxy-1-bromo-naphthalene
4-Bromo-naphthalen-2-ol (5.0 g, 22.41 mmol) is dissolved in dry DMF (50 ml) under an atmosphere of argon. Sodium hydride (986 mg of a 60% suspension in mineral oil, 592 mg, 24.65 mmol) is added and the mixture is stirred at 50° C. for 1 h. After re-cooling to RT, benzyl bromide (3.46 ml, 4.98 g, 29.14 mmol) and tetrabutyl ammoniumiodide (828 mg, 2.24 mmol) are added. After 16 h at RT, the reaction mixture is diluted with EtOAc. The solution is washed twice with semi-concentrated brine (back extracted). The combined organic layers are dried over $Na_2SO_4$, the solvent is removed, and the residue is purified by FCC (hexane/EtOAc 100:0 to 95:5 to 90:10) to yield the title compound. $^1$H NMR (CDCl$_3$, 400 MHz) δ 5.22 (s, 2H), 7.25 (d, J=1.5 Hz, 1H), 7.45 (m, 7H), 7.64 (d, J=2.4, 1H), 7.75 (d, J=7.8, 1H), 8.17 (d, J=7.8, 1H); ES-MS: 312 [M+H]$^+$.

By following procedure of example 20, the compounds of formula I wherein R is a residue of formula (b), as indicated in Table 2 may be obtained.

TABLE 2

| Example | R$_4$ | R$_a$ | M.S. Data |
|---|---|---|---|
| 21 | 3-R-methyl-piperazin-1-yl | CH$_3$ | MH$^+$ 452 |
| 22 | -(4,7-diaza-spiro[2.5]oct-7-yl) | CH$_3$ | MH$^+$ 464 |
| 23 | -(4,7-diaza-spiro[2.5]oct-7-yl) | H | MH$^+$ 450 |
| 24 | 3-R-methyl-piperazin-1-yl | H | MH$^+$ 438 |
| 25 | 3-S-methyl-piperazin-1-yl | CH$_3$ | MH$^+$ 452 |
| 26 | 3-S-methyl-piperazin-1-yl | H | MH$^+$ 438 |
| 27 | 4-methyl-3-S-methyl-piperazin-1-yl | CH$_3$ | MH$^+$ 466 |
| 28 | 4-methyl-3-S-methyl-piperazin-1-yl | H | MH$^+$ 452 |

By following the procedure as disclosed above or in Example 56 in WO02/38561, but using the appropriate starting materials the compounds of formula I wherein R is a residue of formula (c), as indicated in Table 3 below may be obtained.

TABLE 3

| Ex. | R$_{14}$ | R$_{15}$ in 4 | R$_{16}$ in 5 | R$_a$ | R$_b$ | M.S. Data |
|---|---|---|---|---|---|---|
| 29 | -(4-methyl-piperazin-1-yl) | Cl | CH$_3$ | H | H | MH$^+$ 437 |
| 30 | -(4-methyl-piperazin-1-yl) | Br | H | H | H | MH$^+$ 469 |
| 31 | -(4-methyl-piperazin-1-yl) | Br | CH$_3$ | H | H | MH$^+$ 483 |
| 32 | -(4-methyl-piperazin-1-yl) | Br | H | CH$_3$ | H | MH$^+$ 483 |
| 33 | -(4-methyl-piperazin-1-yl) | CF$_3$ | H | H | H | MH$^+$ 457 |
| 34 | -(4-methyl-piperazin-1-yl) | CF$_3$ | H | CH$_3$ | H | MH$^+$ 471 |
| 35 | 3-R-methyl-piperazin-1-yl | Cl | CH$_3$ | H | H | MH$^+$ 437 |
| 36 | -(4,7-diaza-spiro[2.5]oct-7-yl) | Cl | CH$_3$ | H | H | MH$^+$ 449 |
| 37 | 1-piperazinyl | Cl | CH$_3$ | H | H | MH$^+$ 423 |
| 38 | 4-methyl-3-R-methyl-piperazin-yl | Cl | CH$_3$ | H | H | MH$^+$ 451 |
| 39 | 3-R-methoxyethyl-piperazin-1-yl | Cl | CH$_3$ | H | H | MH$^+$ 481 |
| 40 | 3-R-ethyl-piperazin-1-yl | Cl | CH$_3$ | H | H | MH$^+$ 451 |
| 41 | 3-R-benzyl-piperazin-1-yl | Cl | CH$_3$ | H | H | MH$^+$ 514 |
| 42 | 3-S-methyl-piperazin-1-yl | Cl | CH$_3$ | H | H | MH$^+$ 437 |
| 43 | 4-methyl-piperazin-1-yl | Cl | CH$_3$ | H | CH$_2$—CH$_2$—CH$_3$ | MH$^+$ 479 |
| 44 | 3-CH$_2$F-piperazin-1-yl | Cl | CH$_3$ | H | H | MH$^+$ 453 |
| 45 | 4-methyl-piperazin-1-yl | Cl | CH$_3$ | H | F | MH$^+$ 455 |
| 46 | 4-methyl-piperazin-1-yl | Cl | CH$_3$ | H | CH(CH$_3$)$_2$ | MH$^+$ 479 |
| 47 | 4-methyl-piperazin-1-yl | Cl | CH$_3$ | H | Cl | MH$^+$ 471 |
| 48 | 4-methyl-piperazin-1-yl | Cl | CH$_3$ | H | OCH$_3$ | MH$^+$ 467 |
| 49 | 4-methyl-piperazin-1-yl | Cl | CH$_3$ | H | CH$_3$ | MH$^+$ 451 |
| 50 | 4-methyl-piperazin-1-yl | Cl | CH$_3$ | H | CH$_2$—CH$_3$ | MH$^+$ 465 |
| 51 | 4-methyl-piperazin-1-yl | CF$_3$ | H | H | CH$_2$—CH$_3$ | MH$^+$ 485 |
| 52 | 4-methyl-piperazin-1-yl | CF$_3$ | H | H | CH$_3$ | MH$^+$ 471 |
| 53 | 4-methyl-piperazin-1-yl | F | H | H | H | MH$^+$ 407 |
| 54 | 4-methyl-piperazin-1-yl | F | H | H | CH$_3$ | MH$^+$ 421 |
| 55 | 4-methyl-piperazin-1-yl | F | H | H | CH$_2$—CH$_3$ | MH$^+$ 435 |
| 56 | 4-methyl-piperazin-1-yl | F | CH$_2$—CH$_3$ | H | CH$_3$ | MH$^+$ 449 |
| 57 | 4-methyl-piperazin-1-yl | F | CH$_2$—CH$_3$ | H | H | MH$^+$ 435 |
| 58 | 4-methyl-piperazin-1-yl | F | CH$_2$—CH$_3$ | H | CH$_2$—CH$_3$ | MH$^+$ 463 |
| 59 | 4-methyl-piperazin-1-yl | F | CH$_3$ | H | H | MH$^+$ 421 |
| 60 | 4-methyl-piperazin-1-yl | F | CH$_3$ | H | CH$_3$ | MH$^+$ 435 |
| 61 | 4-methyl-piperazin-1-yl | F | CH$_3$ | H | CH$_2$—CH$_3$ | MH$^+$ 449 |

By following the procedure as disclosed above or in Example 163 in WO 02138561, but using the appropriate starting material the compounds of formula I wherein R is a residue of formula (d), as indicated in Table 4 below, may be obtained.

TABLE 4

| Example | R$_8$ | R$_a$ | M.S. Data |
|---|---|---|---|
| 62 | 3-S-methyl-piperazin-1-yl | CH$_3$ | MH$^+$ 452 |
| 63 | 3-R-methyl-piperazin-1-yl | H | MH$^+$ 438 |
| 64 | 3-R-methyl-piperazin-1-yl | CH$_3$ | MH$^+$ 452 |
| 65 | 4-benzyl-1-piperazinyl | H | MH$^+$ 514 |
| 66 | 4-benzyl-1-piperazinyl | CH$_3$ | MH$^+$ 528 |
| 67 | 1-piperazinyl | CH$_3$ | MH$^+$ 438 |
| 68 | 1-piperazinyl | H | MH$^+$ 424 |

EXAMPLE 69

3-[3-(4,7-Diaza-spiro[2.5] oct-7-yl)-isoquinolin-1-yl]-4-7-methyl-1H-indol-3-yl)-pyrrole-2,5-dione

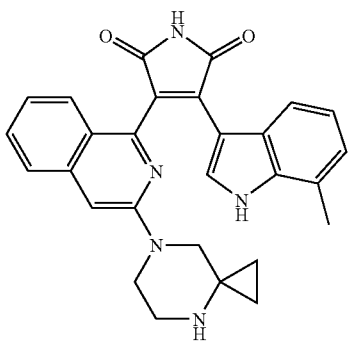

2-[3-(4,7-Diaza-spiro[2.5] oct-7-yl)-isoquinolin-1-yl]-acetamide (4.95 g, 16.70 mmol) and (7-Methyl-1H-indol-3-yl)-oxo-acetic acid methyl ester (5.44 g, 25.05 mmol) are azeotroped twice with dry THF. Dry THF (100 ml) is then added, and under an atmosphere of argon KOtBu (1.0 M in THF, 50 ml, 50 mmol) is added dropwise during 20 min. After an additional 90 min, TLC analysis indicates complete conversion of starting materials. The reaction mixture is diluted with $H_2O$ and extracted twice with EtOAc. The combined organic layers are washed twice with saturated aq $NH_4Cl$ solution (back extracted), dried over $Na_2SO_4$ and concentrated. Purification by FCC ($CH_2Cl_2$/MeOH 100:0 to 98:2 to 96:4 to 94:6 to 92:8 to 90:10) yields the title compound, which is converted to its acetate salt by concentration of a EtOH/AcOH solution. $^1$H NMR (DMSO, 400 MHz) δ 0.26-053 (br, 4 H), 1.89 (s, 3H, $CH_3COOH$), 2.36 (s, 3H), 2.80 (br m, 2 H), 3.15-3.48 (br m, 2H), 6.14 (d, J=8.2 HZ, 1H), 6.44 (dd, J=8.2/7.4 Hz, 1H), 6.75 (d, J=7.4 Hz, 1H), 7.00 (s, 1H), 7.02 (dd, J=8.2/8.2 Hz, 1H), 7.40 (dd, J=8.2/8.2 Hz, 1H), 7.59 (d, J=8.2 Hz, 1H), 7.63 (d, J=8.2 Hz, 1H), 7.63 (d, J=8.2 Hz, 1H), 7.97 (d, J=2.9 Hz, 1H), 11.04-11.21 (br, 1H), 11.86 (d, J=2.9 Hz, 1H); ES-MS: 464 [M+H]$^+$.

2-[3-(4,7-Diaza-spiro[2.5] oct-7-yl)-isoquinolin-1-yl]-acetamide used as starting material may be prepared as follows:

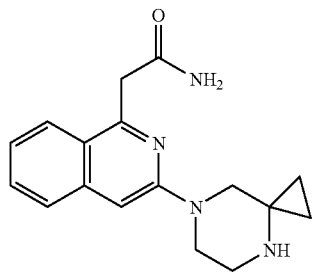

a) 2-[3-(4-Benzyl-4,7-diaza-spiro[2.5] oct-7-yl)-isoquinolin-1-yl]-acetamide (490 mg, 1.27 mmol) is dissolved in absolute MeOH (5 ml). Pd on charcoal (140 mg) is added, as well as ammonium formate (200 mg, 3.17 mmol). After refluxing for 1 h (T=75° C.), an additional charge of ammonium formate (200 mg, 3.17 mmol) is added. 1 h later, TLC analysis indicates complete conversion of the starting material. After filtration and concentration, the residue is taken up in $CH_2Cl_2$ and washed with water (pH 10 by addition of 2 N NaOH). The organic layer is dried over $Na_2SO_4$ and the solvent is removed. Purification by FCC (EtOAc/AcOH/$H_2O$ 750:83:68 to 700:110:90 to 650:130:120 to 600:150:150) affords the title compound as its bis-acetate salt. $^1$H NMR (DMSO, 400 MHz) δ 0.46-0.52 (m, 4H), 2.88 (t, J=5.5, 2H), 3.35 (s, 2H), 3.49 (t, J=5.5, 2H), 3.94 (s, 2H), 6.77 (s, 1H), 7.00 (br s, 1H), 7.18-7.25 (m, 1H), 7.45-7.56 (m, 2H), 7.60-7.65 (m, 1H), 7.95 (d, J=9.9, 1H). ES-MS: 297 [M+H]$^+$.

b) 2-[3-(4-Benzyl-4,7-diaza-spiro[2.5] oct-7-yl)-isoquinolin-1-yl]-acetamide

[3-(4-Benzyl-4,7-diaza-spiro[2.5] oct-7-yl)-isoquinolin-1-yl]-acetic acid ethyl ester (700 mg, 1.68 mmol) is dissolved in dry DMF under an atmosphere of argon. Formamide (224 μl, 254 mg, 5.64 mmol) is added, and the reaction mixture is heated to 105° C. At this temperature, NaOMe (312 μl of a 5.4 M solution in MeOH, 91 mg, 1.68 mmol) is added dropwise during 20 minutes. After 30 minutes at 105° C., TLC analysis indicates complete conversion of starting material. Cooling the reaction mixture to RT is followed by addition of water and extraction with EtOAc. The organic layers are washed with $H_2O$ (twice), dried over $Na_2SO_4$ and concentrated. The residue is purified by FCC (hexanes/EtOAc 1:1 to 1:3 to 0:100 to EtOAc/MeOH 98:2) to afford the title compound. $^1$H NMR (DMSO, 400 MHz) δ 0.68-0.70 (m, 2H), 0.82-0.88 (m, 2H), 3.08 (t, J=4.4, 2H), 3.45 (s, 2H), 3.58 (t, J=4.4, 2H), 3.96 (s, 2H), 4.27 (s, 2H), 5.3-5.5 (br, 1H), 6.55-6.7 (br, 1H), 6.72 (s, 1H), 7.26-7.36 (m, 6H), 7.51 (t, J=8.8, 1H), 7.60 d, J=9.9, 1H), 8.02 (d, J=9.9, 1H); ES-MS: 387 [M+H]$^+$.

c) [3-(4-Benzyl-4,7-diaza-spiro[2.5] oct-7-yl)-isoquinolin-1-yl]-acetic acid ethyl ester (3-Chloro-isoquinolin-1-yl)-acetic acid ethyl ester (2.50 g, 10.01 mmol), 4-benzyl-4,7-diaza-spiro[2.5]octane (2.23 g, 11.01 mmol), NaOtBu (1.06 g, 11.01 mmol), BINAP (249 mg, 0.40 mmol) and Palladium (II)-acetate (180 mg, 0.80 mmol) are mixed under argon. After addition of degassed, dry dioxane (36 ml), the suspension is heated to 85° C. After 25 minutes at 85° C., HPLC analysis indicates a conversion of 71%. The mixture is cooled to RT, diluted with EtOAc, and washed with $H_2O$ and sat. aq. $NH_4Cl$ (back extracted). The combined organic layers are dried over $Na_2SO_4$, the solvent is removed and the residue purified by FCC (hexane/EtOAc 100:0 to 96:4 to 93:7 to 90:10 to 85:15) to afford the title compound. $^1$H NMR (DMSO, 400 MHz) δ 0.58-0.61 (m, 2H), 0.70-0.73 (m, 2H), 1.18 (t, J=8.8, 3H), 2.98 (t, J=5.5, 2H), 3.39 (s, 2H), 3.49 (t, J=5.5, 2H), 3.86 (s, 2H), 4.12 (s, 2H), 4.12 (q, J=8.8, 2H), 5.59 (s, 1H), 7.14-7.19 (m, 6H), 7.39 (t, J=8.8, 1H), 7.51 (d, J=9.9, 1H), 7.78 (d, J=9.9, 1H); ES-MS: 417 [M+H]$^+$.

d) (3-Chloro-isoquinolin-1-yl)-acetic acid ethyl ester 1,1,1,3,3,3-Hexamethyl-disilazane (27.4 ml, 20.37 g, 126.2 mmol) are dissolved in dry toluene (150 ml). After cooling to −78° C., n-BuLi (79 ml of a 1.6 M solution in hexanes, 126.2 mmol) is slowly added during 20 minutes. The white suspension is stirred at −78° C. for 15 minutes and at RT for 15 minutes, after which time a clear bright yellow solution is obtained. This solution is canulated into a second two-necked flask, containing Pd$_2$(dba)$_3$ (1.39 g, 1.51 mmol) and (2'-Dicyclohexylphosphanyl-biphenyl-2-yl)-dimethyl-amine (1.25 g, 3.18 mmol). After stirring at RT for 10 minutes, the clear dark red solution is cooled to −10° C. Acetic acid tert-butyl ester (15.7 ml, 13.5 g, 116.1 mmol) is added during 5 min. After 10 minutes at −10° C. 1,3-

Dichloro-isoquinoline (10.0 g, 50.49 mmol) is added in one portion. The dark red solution is allowed to warm to RT. After 30 minutes at RT, TLC analysis indicates complete conversion of the starting material. The reaction mixture is filtered through a 2-cm pad of silica, which is rinsed with EtOAc/MeOH 98:2. After concentration, the residue is purified by FCC (toluene/$CH_2Cl_2$ 2:1 to toluene/EtOAc 100:0 to 99:1 to 98:2 to 97:3 to 96:4 to 94:6 to 90:10) to afford (3-Chloro-isoquinolin-1-yl)-acetic acid tert.-butyl ester. This compound is dissolved in a saturated ethanolic solution of HCl (200 ml) and refluxed for 15 minutes. Concentration affords the title compound in quantitative yield. $^1$H NMR (DMSO, 400 MHz) δ 1.17 (t, J=8.8, 3H), 4.11 (q, J=8.8, 2H), 4.28 (s, 2H), 7.51-7.57 (m, 1H), 7.61 (s, 1H), 7.61-7.66 (m, 1H), 7.72 (d, J=8.8, 1H), 7.98 (d, J=8.8, 1H); ES-MS: 250 [M+H]$^+$.

By following the procedure of Example 69 but using the appropriate starting materials, the compounds of formula I wherein R is residue of formula (e), as indicated in Table 5 below, may be obtained.

TABLE 5

| Example | $R_9$ | $R_a$ | $R_b$ | M.S. Data |
|---|---|---|---|---|
| 70 | -(4,7-diaza-spiro[2.5]oct-7-yl) | $CH_3$ | H | MH$^+$ 465 |
| 71 | 3-ethyl-piperazin-1-yl | $CH_3$ | H | MH$^+$ 467 |
| 72 | -(4,7-diaza-spiro[2.5]oct-7-yl) | H | H | MH$^+$ 451 |
| 73 | 3-ethyl-1-piperazinyl | H | H | MH$^+$ 453 |
| 74 | 3-R-methyl-piperazin-1-yl | $CH_3$ | H | MH$^+$ 453 |
| 75 | 3-R-methyl-piperazin-1-yl | H | H | MH$^+$ 439 |
| 76 | 3-S-methyl-piperazin-1-yl | $CH_3$ | H | MH$^+$ 453 |
| 77 | 3-S-methyl-piperazin-1-yl | H | H | MH$^+$ 439 |
| 78 | 4-methyl-3-S-methyl-piperazin-1-yl | $CH_3$ | H | MH$^+$ 467 |
| 79 | 4-methyl-3-S-methyl-piperazin-1-yl | H | H | MH$^+$ 453 |
| 80* | 4,7-diaza-spiro[2.5]7ct-7-yl | $CH_3$ | H | MH$^+$ 464 |
| 81 | 4,7-diaza-spiro[2.5]7ct-7-yl | H | F | MH$^+$ 479 |
| 82 | 4,7-diaza-spiro[2.5]7ct-7-yl | $CH_2$—$CH_3$ | H | MH$^+$ 479 |
| 83 | 4,7-diaza-spiro[2.5]7ct-7-yl | H | $CH(CH_3)_2$ | MH$^+$ 495 |
| 84 | 4,7-diaza-spiro[2.5]7ct-7-yl | H | $OCH_3$ | MH$^+$ 471 |
| 85 | 4,7-diaza-spiro[2.5]7ct-7-yl | $CH_3$ | $CH_2$—$CH_3$ | MH$^+$ 451 |
| 86 | 4,7-diaza-spiro[2.5]7ct-7-yl | H | $CH_2$—$CH_3$ | MH$^+$ 465 |
| 87 | 4,7-diaza-spiro[2.5]7ct-7-yl | $CH(CH_3)_2$ | H | MH$^+$ 451 |
| 88 | 4,7-diaza-spiro[2.5]7ct-7-yl | $CH_3$ | $CH_3$ | MH$^+$ 479 |
| 89 | 4,7-diaza-spiro[2.5]7ct-7-yl | $CH_3$ | Cl | MH$^+$ 499 |
| 90 | 4,7-diaza-spiro[2.5]7ct-7-yl | H | Cl | MH$^+$ 485 |
| 91 | 4,7-diaza-spiro[2.5]7ct-7-yl | $CH_2$—$CH_3$ | $CH_3$ | MH$^+$ 492 |
| 92 | 3-ethyl-piperazin-1-yl | $CH_2$—$CH_3$ | $CH_2$—$CH_3$ | MH$^+$ 494 |

*The compound of Example 80 is converted into its bis-trifluoroacetate or acetate salt.

The compounds of formula I in free form or in pharmaceutically acceptable salt form exhibit valuable pharmacological properties, e.g. inhibiting Protein Kinase C (PKC), e.g. PKC isoforms like α, β, δ, ε, η or θ activity, inhibiting T-cell activation and proliferation, e.g. by inhibiting production by T-cells or cytokines, e,g, IL-2, by inhibiting the proliferative response of T-cells to cytokines, e.g. IL-2, e.g. as indicated in in vitro and in vivo tests and are therefore indicated for therapy.

A. In Vitro

1. Protein Kinase C Assay

The compounds of formula I are tested for their activity on different PKC isoforms according to a published method (D. Geiges et al. Biochem. Pharmacol. 1997;53:865-875) The assay is performed in a 96-well polypropylene microtiterplate (Costar 3794) that has been previously siliconized with Sigmacote (Sigma SL-2). The reaction mixture (50 µl) contains 10 µl of the relevant PKC isozyme together with 25 µl of the test compound and 15 µl of a mix solution that contains 200 µg/ml protamine sulfate, 10 mM Mg(NO$_3$)$_2$, 10 µM ATP (Boehringer 519987) and 3750 Bq of $^{33}$P-ATP (Hartmann Analytic SFC301, 110TBq/mmol) in 20 mM Tris-buffer pH 7.4+0.1% BSA. Incubation is performed for 15 min. at 32° C. in a microtiterplate shaking incubator (Biolabo Scientific Instruments). Reaction is stopped by adding 10 µl of 0.5 M Na$_2$EDTA, pH 7.4. 50 µl of mixture are pipetted onto a pre-wetted phosphocellulose paper (Whatmann 3698-915) under gentle pressure. Non-incorporated ATP is washed away with 100 µl bi-dist H$_2$O. The paper is washed twice in 0.5% H$_3$PO$_4$ for 15 min followed by 5 min in EtOH. Thereafter the paper is dried and placed in an omnifilter (Packard 6005219), and overlayed with 10 µl/well of Microscint-O (Packard 6013611) before counting in a Topcount radioactivity counter (Packard). IC$_{50}$ measurement is performed on a routine basis by incubating a serial dilution of inhibitor at concentrations ranging between 1-1000 µM according to the method described above. IC$_{50}$ values are calculated from the graph by sigmoidal curve fitting.

2. Protein Kinase C θ Assay

Human recombinant PKCθ is used under the assay conditions as described above. In this assay, compounds of formula I inhibit PKC θ with an IC$_{50}$≦1 µM. Compound of Examples 33 and 69 inhibit PKCθ in this assay with an IC$_{50}$ 6.8 and 12.1 nM, respectively.

3. Protein Kinase Cα Assay

Human recombinant PKCα was obtained from Oxford Biomedical Research and is used under the assay conditions as described under Section A.1 above. In this assay, compounds of formula I inhibit PKC θ with an IC$_{50}$≦1 µM. Compound of Example 29 inhibits PKCα in this assay with an IC$_{50}$ of 4.3 nM.

4. Protein Kinase Cβ1 Assay

Human recombinant PKCβ1 was obtained from Oxford Biomedical Research and is used under the assay conditions as described under Section A.1 above. In this assay, compounds of formula I inhibit PKC θ with an IC$_{50}$≦1 µM. Compound of Example 33 inhibits PKCβ1 in this assay with an IC$_{50}$ of 19.6 nM.

5. Protein Kinase Cδ Assay

Human recombinant PKCδ was obtained from Oxford Biomedical Research and is used under the assay conditions as described under Section A.1 above. In this assay, compounds of formula I inhibit PKC θ with an $IC_{50} \leq 1$ μM. Compound of Example 29 inhibits PKCδ in this assay with an $IC_{50}$ of 20 nM.

6. Protein Kinase Cε Assay

Human recombinant PKCε was obtained from Oxford Biomedical Research and is used under the assay conditions as described under Section A.1 above. In this assay, compounds of formula I inhibit PKC θ with an $IC_{50} \leq 1$ μM. Compound of Example 69 inhibits PKCε in this assay with an $IC_{50}$ of 18 nM.

7. Protein Kinase Cη Assay

Human recombinant PKCη was obtained from PanVera and is used under the assay conditions as described under Section A.1 above. In this assay, compounds of formula I inhibit PKC θ with an $IC_{50} \leq 1$ μM. Compound of Example 29 inhibits PKCη in this assay with an $IC_{50}$ of 27.4 nM.

8. CD28 Costimulation Assay

The assay is performed with Jurkat cells transfected with a human interleukin-2 promoter/reporter gene construct as described by Baumann G et al. in Transplant. Proc. 1992; 24:43-8, the β-galactosidase reporter gene being replaced by the luciferase gene (de Wet J., et al., Mol. Cell Biol. 1987, 7(2), 725-737). Cells are stimulated by solid phase-coupled antibodies or phorbol myristate acetate (PMA) and the $Ca^{++}$ ionophore ionomycin as follows. For antibody-mediated stimulation Microlite TM1 microtiter plates (Dynatech) are coated with 3 μg/ml goat anti-mouse IgG Fc antibodies (Jackson) in 55 μl phosphate-buffered saline (PBS) per well for three hours at RT. Plates are blocked after removing the antibodies by incubation with 2% bovine serum albumin (BSA) in PBS (300 μl per well) for 2 hours at RT. After washing three times with 300 μl PBS per well, 10 ng/ml anti-T cell receptor antibodies (WT31, Becton & Dickinson) and 300 ng/ml anti-CD28 antibodies (15E8) in 50 μl 2% BSA/PBS are added as stimulating antibodies and incubated overnight at 4° C. Finally the plates are washed three times with 300 μl PBS per well. Seven three-fold serial dilutions of test compounds in duplicates in assay medium (RPMI 1640/10% fetal calf serum (FCS) containing 50 μM 2-mercaptoethanol, 100 units/ml penicillin and 100 μg/ml streptomycin) are prepared in separate plates, mixed with transfected Jurkat cells (clone K22 290_H23) and incubated for 30 minutes at 37° C. in 5% $CO_2$. 100 μl of this mixture containing $1 \times 10^5$ cells are then transferred to the antibody-coated assay plates. In parallel 100 μl are incubated with 40 ng/ml PMA and 2 μM ionomycin. After incubation for 5.5 hours at 37° C. in 5% $CO_2$, the level of luciferase is determined by bioluminescence measurement. The plates are centrifuged for 10 min at 500 g and the supernatant is removed by flicking. Lysis buffer containing 25 mM Tris-phosphate, pH 7.8, 2 mM DTT, 2 mM 1.2-diaminocyclohexane-N,N,N',N-tetraacetic acid, 10% (v/v) glycerol and 1% (v/v) Triton X-100 is added-(20 μl per well). The plates are incubated at RT for 10 minutes under constant shaking. Luciferase activity is assessed with a bioluminescence reader (Labsystem, Helsinki, Finland) after automatic addition of 50 μl per well luciferase reaction buffer containing 20 mM Tricine, 1.07 mM $(MgCO_3)_4Mg(OH)_2 \times 5H_2O$, 2.67 mM $MgSO_4$, 0.1 mM EDTA, 33.3 mM DTT, 270 μM coenzyme A, 470 μM luciferin (Chemie Brunschwig AG), 530 μM ATP, pH 7.8. Lag time is 0.5 seconds, total measuring time is 1 or 2 seconds. Low control values are light units from anti-T cell receptor- or PMA-stimulated cells, high controls are from anti-T cell receptor/anti-CD28- or PMA/ionomycin-stimulated cells without any test sample. Low controls are subtracted from all values. The inhibition obtained in the presence of a test compound is calculated as percent inhibition of the high control. The concentration of test compounds resulting in 50% inhibition ($IC_{50}$) is determined from the dose-response curves. In this assay, compounds of formula I inhibit anti-T cell receptor/anti-CD28 and PMA/ionomycin stimulated Jurkat cells with an $IC_{50} \leq 1$ μM. Compound of Example 29 has an $IC_{50}$ of 20 nM in this assay.

9. Allogeneic Mixed Lymphocyte Reaction (MLR)

The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice ($1.6 \times 10^5$ cells from each strain per well in flat bottom tissue culture microtiter plates, $3.2 \times 10^5$ in total) are incubated in RPMI medium containing 10% FCS, 100 U/ml penicillin, 100 μg/ml streptomycin (Gibco BRL, Basel, Switzerland), 50 μM 2-mercaptoethanol (Fluka, Buchs, Switzerland) and serially diluted compounds. Seven three-fold dilution steps in duplicates per test compound are performed. After four days of incubation 1 μCi $^3$H-thymidine is added. Cells are harvested after an additional five-hour incubation period, and incorporated $^3$H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition ($IC_{50}$ values) are determined. In this assay, Compound of Example 29 has an $IC_{50}$ of 28 nM. Compounds of formula I also exhibit $IC_{50}$ values in the nM range when tested in the human MLR.

10. Inhibition of GSK-3β

The GSK-3β binding assay is performed in 50 μl reactions in 96 well polypropylene plate, each reaction containing 20 mM magnesium chloride, 40 μM ATP, 2 mM DTT, 88.5 μM biotinylated and phosphorylated CREB-peptide substrate (biotin-KRREILSRRPS($PO_4$)YR—OH; Q. M. Wang et al., J. Biol. Chem. 269, 14566-14574, 1994), [γ-$^{33}$P]ATP (1 μCi) and 2 μl of the compound to be tested in DMSO(various concentrations). 15 μl of GSK-3β (various concentrations) is added and the mixture is incubated at 30° C. for 1 hour. The reaction is stopped by transferring 25 μl of the mixture to a phosphocellulose plate containing 130 μl of 1.85% phosphoric acid. The free radionucleotides in the membrane are washed off under vacuum with 1.85% phosphoric acid (5 times). After the last wash, the plate is transferred to an adaptor plate and 50 μl of scintillation cocktail (Microscint-20, Packard, cat. a 20-133) is added to each well and the amount of radioactivity is counted in a top counter. Compounds of formula I are active in this assay. Compounds of formula I may also be tested in other standard GSK-3β binding assays using other substrates, e.g. as commercially available.

B. In Vivo

Rat Heart Transplantation

The strain combination used: Male Lewis ($RT^1$ haplotype) and BN ($RT^1$ haplotype). The animals are anaesthetised using inhalational isofluorane. Following heparinisation of the donor rat through the abdominal inferior vena cava with simultaneous exsanguination via the aorta, the chest is opened and the heart rapidly cooled. The aorta is ligated and divided distal to the first branch and the brachiocephalic trunk is divided at the first bifurcation. The left pulmonary artery is ligated and divided and the right side divided but left open. All other vessels are dissected free, ligated and divided and the donor heart is removed into iced saline.

The recipient is prepared by dissection and cross-clamping of the infra-renal abdominal aorta and vena cava. The graft is implanted with end-to-side anastomoses, using 10/0 monofilament suture, between the donor brachiocephalic trunk and the recipient aorta and the donor right pulmonary artery to the recipient vena cava. The clamps are removed, the graft tethered retroabdominally, the abdominal contents washed with warm saline and the animal is closed and allowed to recover under a heating lamp. Graft survival is monitored by daily palpation of the beating donor heart through the abdominal wall. Rejection is considered to be complete when heart beat stops. Increases of graft survival are obtained in animals treated with a compound of formula I administered orally at a daily dose of 1 to 30 mg/kg bid.

Graft v. Host Model

Spleen cells ($2 \times 10^7$) from Wistar/F rats are injected subcutaneously into the right hind footpad of (Wistar/F× Fischer 344)$F_1$ hybrid rats. The left footpad is left untreated. The animals are treated with the test compounds on 4 consecutive days (0-3). The popliteal lymph nodes are removed on day 7, and the weight differences between two corresponding lymph nodes are determined. The results are expressed as the inhibition of lymph node enlargement (given in percent) comparing the lymph node weight differences in the experimental groups to the weight difference between the corresponding lymph nodes from a group of animals left untreated with a test compound. In this assay, an inhibition of 100% is obtained with compound of Example 29 when administered at a dose of 30 mg/kg/day bid.

The compounds of formula I are, therefore, useful in the treatment and/or prevention of diseases or disorders mediated by T lymphocytes and/or PKC, e.g. acute or chronic rejection of organ or tissue allo- or xenografts, graft versus host diseases, atherosclerosis, vascular occlusion due to vascular injury such as angioplasty, restenosis, obesity, syndrome X, impaired glucose tolerance, polycystic ovary syndrome, hypertension, heart failure, chronic obstructive pulmonary disease, CNS diseases such as Alzheimer disease or amyotrophic lateral sclerosis, cancer, infectious diseases such as AIDS, septic shock or adult respiratory distress syndrome, ischemia/reperfusion injury e.g. myocardial infarction, stroke, gut ischemia, renal failure or hemorrhage shock, or traumatic shock, e.g. traumatic brain injury. The compounds of formula I are also useful in the treatment and/or prevention of T-cell mediated acute or chronic inflammatory diseases or disorders or autoimmune diseases e.g. rheumatoid arthritis, osteoarthritis, systemic lupus erythematosus, Hashimoto's thyroidis, multiple sclerosis, myasthenia gravis, diabetes type I or II and the disorders associated therewith, e.g. angiopathy, diabetic proliferative retinopathy, diabetic macular edema, nephropathy, neuropathy and dawn phenomenon, respiratory diseases such as asthma or inflammatory lung injury, inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases, e.g. Sjoegren's syndrome, keratoconjunctivitis or uveitis, inflammatory bowel disease, Crohn's disease or ulcerative colitis. For the above uses the required dosage will of course vary depending on the mode of administration, the particular condition to be treated and the effect desired. In general, satisfactory results are indicated to be obtained systemically at daily dosages of from about 0.1 to about 100 mg/kg body weight. An indicated daily dosage in the larger mammal, e.g. humans, is in the range from about 0.5 mg to about 2000 mg, conveniently administered, for example, in divided doses up to four times a day or in retard form.

The compounds of formula I may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of formula I in free form or in pharmaceutically acceptable salt form in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

Topical administration is e.g. to the skin. A further form of topical administration is to the eye.

The compounds of formula I may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by T lymphocytes and/or PKC or GSK-3β, e.g. such as indicated above, in a subject in need of such treatment, which method comprises administering to said subject an effective amount of a compound of formula I or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of formula I or a pharmaceutically acceptable salt thereof;

2. A compound of formula I, in free form or in a pharmaceutically acceptable salt form for use as a pharmaceutical, e.g. in any of the methods as indicated under 1.1 and 1.2 above.

3. A pharmaceutical composition, e.g. for use in any of the methods as in 1.1 and 1.2 above comprising a compound of formula I in free form or pharmaceutically acceptable salt form in association with a pharmaceutically acceptable diluent or carrier therefor.

4. A compound of formula I or a pharmaceutically acceptable salt thereof for use in the preparation of a pharmaceutical composition for use in any of the method as in 1.1 and 1.2 above.

Compounds of formula I may be administered as the sole active ingredient or together with other drugs in immunomodulating regimens or other anti-inflammatory agents e.g. for the treatment or prevention of allo- or xenograft acute or chronic rejection or inflammatory or autoimmune disorders. For example, they may be used in combination with cyclosporines, or ascomycines or their immunosuppressive analogs or derivatives, e.g. cyclosporin A, ISA Tx247, FK-506, ABT-281, ASM 981; an mTOR inhibitor, e.g. rapamycin, 40-O-(2-hydroxy)ethyl-rapamycin, CC1779, ABT578 or a rapalog, e.g. AP23573 etc.; corticosteroids;

cyclophosphamide; azathioprene; methotrexate; an EDG receptor agonist having accelerating lymphocyte homing properties, e.g. FTY 720 or an analogue thereof; leflunomide or analogs thereof; mizoribine; mycophenolic acid; mycophenolate mofetil; 15-deoxyspergualine or analogs thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands, e.g. CD154; or other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y, or other adhesion molecule inhibitors, e.g. mAbs or low molecular weight inhibitors including LFA-1 antagonists, Selectin antagonists and VLA-4 antagonists. Compounds of formula I may also be administered together with an antiproliferative drug, e.g. a chemotherapeutic drug, e.g. as used in cancer treatment, including but not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide, or with an anti-diabetic drug, an insulin secretagogue or insulin secretion enhancer, e.g. a sulphonyl urea, e.g. tolbutamide, chlorpropamide, tolazamide, acetohexamide, 4-chloro-N-[(1-pyrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide or tolylcyclamide, an oral insulinotropic agent derivative, e.g. a short acting insulin enhancer, e.g. meglitinide, repaglinide, a phenyl acetic acid derivative, e.g.nateglinide, a DPP IV inhibitor, e.g. 1-{2-[(5-cyanopyrdin-2-yl)amino]ethylamino}acetyl-(2S)-cyano-pyrrolidine dihydrochloride, LAF237, GLP-1 or a GLP-1 agonist analog, or an insulin sensitizer e.g. a peroxisome proliferator activated receptor γ agonist (PPARγ), e.g. a glitazone, a non-glitazone type such as a N-(2-benzoylphenyl)-L-tyrosine analogue, e.g. GI-262570, or an oxolidinedione, e.g. JTT501, a dual PPARγ/PPARα agonist, e.g. DRF-554158, NC-2100 or NN-622, a retinoid X receptor agonist or a rexinoid, e.g. 2-[1-(3,5,5,8,8-pentamethyl-5,6,7,8-tetrahydro-2-naphthyl)-cyclopropyl]-pyridine-5-carboxylic acid, 4-[(3,5,5,8,8-pentamethyl-5,6,7,8-tetrahydro-2-naphthyl)-2-carbonyl]-benzoic acid, 9-cis retinoic acid or an analog, derivative or a pharmaceutically acceptable salt thereof, in diabetes therapy, In accordance with the foregoing the present invention provides in a yet further aspect:

5. A method as defined above comprising co-administration, e.g. concomitantly or in sequence, of a therapeutically effective amount of an inhibitor of GSK-3β, PKC or of T-cell activation and proliferation, e.g. a compound of formula I in free form or in pharmaceutically acceptable salt form, and a second drug substance, said second drug substance being an immunosuppressant, immunomodulatory, anti-inflammatory, antiproliferative or anti-diabetic drug, e.g. as indicated above.

6. A therapeutic combination, e.g. a kit, comprising a) an inhibitor of GSK-3β, PKC or of T-cell activation and proliferation, e.g. a compound of formula I in free form or in pharmaceutically acceptable salt form, and b) at least one second agent selected from an immunosuppressant, immunomodulatory, anti-inflammatory, antiproliferative and anti-diabetic drug. Component a) and component b) may be used concomitantly or in sequence. The kit may comprise instructions for its administration.

Where an inhibitor of GSK-3β, PKC or of T-cell activation and proliferation, e.g. a compound of formula I, is administered in conjunction with other immunosuppressive/immunomodulatory, anti-inflammatory, antiproliferative or anti-diabetic therapy, e.g. for preventing or treating acute or chronic graft rejection or inflammatory or autoimmune disorders as hereinabove specified, dosages of the co-administered immunosuppressant, immunomodulatory, anti-inflammatory, antiproliferative or anti-diabetic compound will of course vary depending on the type of co-drug employed, e.g. whether it is a steroid or a cyclosporine, on the specific drug employed, on the condition being treated and so forth.

Compounds of formula I have an interesting pharmacokinetic profile and interesting in vitro and in vivo activities.

The invention claimed is:

1. A method for treating acute or chronic rejection of organ or tissue allo- or xenografts or graft versus host disease in a subject in need of such treatment, which method comprises administering to said subject an effective amount of a compound of formula I

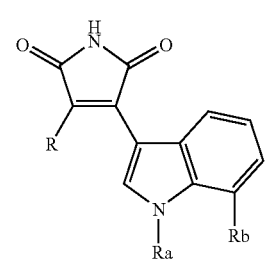

wherein
$R_a$ is H; $CH_3$; $CH_2$-$CH_3$; or isopropyl,
$R_b$ is H; halogen; $C_{1-6}$alkoxy; or $C_{1-6}$alkyl, and either
I. R is a radical of formula (a)

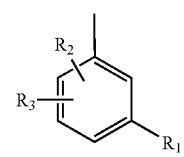

wherein
$R_1$ is piperazin-1-yl optionally substituted by $CH_3$ in position 3 or 4; or 4,7-diaza-spiro [2.5] oct-7-yl;
$R_2$ is Cl; Br; $CF_3$; or $CH_3$; and
$R_3$ is H; $CH_3$; or $CF_3$; $R_2$ being other than $CH_3$ or Cl when $R_3$ is H, $R_a$ is H or $CH_3$, $R_b$ is H and $R_1$ is 4-methyl-1-piperazinyl; or II. R is a radical of formula (b)

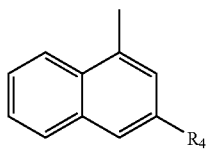

wherein
R$_4$ is piperazin-1-yl substituted in positions 3 and/or 4 by CH$_3$; or 4,7-diaza-spiro [2.5] oct-7-yl; R$_a$ being other than H or CH$_3$ when R$_4$ is 4-methyl-1-piperazinyl; or II. R is a residue of formula (c)

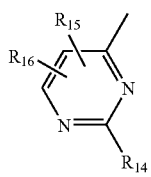

wherein
R$_{14}$ is 4,7-diaza-spiro [2.5] oct-7-yl;
R$_{15}$ is halogen; CF$_3$; or CH$_3$; R$_{15}$ being other than CH$_3$ when R$_{16}$ is CH$_3$, R$_a$ is H or CH$_3$, and R$_b$ is H; and
R$_{16}$ is H; CH$_3$; CH$_2$-CH$_3$; or CF$_3$; R$_{16}$ being other than H when R$_{15}$ is Cl, R$_a$ is H or CH$_3$, and R$_b$ is H; or IV. R is a radical of formula (d)

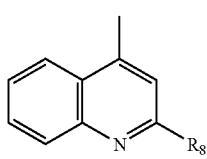

wherein
R$_8$ is 1-piperazinyl, 3-methyl-piperazin-1-yl or 4-benzyl-piperazin-1-yl; or V. R is a radical of formula (e)

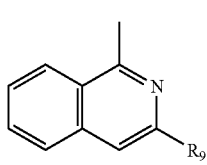

wherein
R$_9$ is 4,7-diaza-spiro [2.5] oct-7-yl; or 1-piperazinyl substituted in position 3 by methyl or ethyl and optionally in position 4 by methyl;
or a pharmaceutically acceptable salt thereof.

2. A method according to claim 1 wherein the compound of formula I is administered by topical route to the skin or to the eye.

3. A method according to claim 1 comprising co-administration, concomitantly or in sequence, of a therapeutically effective amount of a compound of formula I in free form or in pharmaceutically acceptable salt form, and a second drug substance, said second drug substance being an immunosuppressant, immunomodulatory, anti-inflammatory, anti-proliferative or anti-diabetic drug.

4. A pharmaceutical composition comprising a compound of formula I

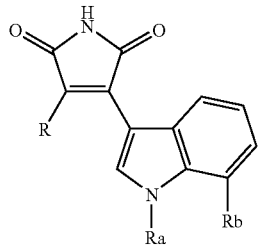

or a pharmaceutically acceptable salt thereof in association with a pharmaceutically acceptable diluent or carrier therefore wherein
R$_a$ is H; CH$_3$; CH$_2$-CH$_3$; or isopropyl,
R$_b$ is H; halogen; C$_{1-6}$alkoxy; or C$_{1-6}$alkyl, and either I. R is a radical of formula (a)

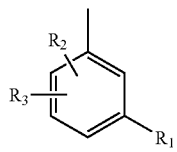

wherein
R$_1$ is piperazin-1-yl optionally substituted by CH$_3$ in position 3 or 4; or 4,7-diaza-spiro [2.5] oct-7-yl;
R$_2$ is Cl; Br; CF$_3$; or CH$_3$; and
R$_3$ is H; CH$_3$; or CF$_3$; R$_2$ being other than CH$_3$ or Cl when R$_3$ is H, R$_a$ is H or CH$_3$, R$_b$ is H and R$_1$ is 4-methyl-1-piperazinyl; or II. R is a radical of formula (b)

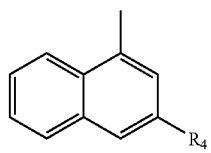

wherein
R$_4$ is piperazin-1-yl substituted in positions 3 and/or 4 by CH$_3$; or 4,7-diaza-spiro [2.5] oct-7-yl; R$_a$ being other than H or CH$_3$ when R$_4$ is 4-methyl-1-piperazinyl; or II. R is a residue of formula (c)

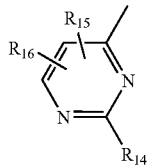

wherein
$R_{14}$ is 4,7-diaza-spiro [2.5] oct-7-yl;
$R_{15}$ is halogen; $CF_3$; or $CH_3$; $R_{15}$ being other than $CH_3$ when $R_{16}$ is $CH_3$, $R_a$ is H or $CH_3$, and $R_b$ is H; and
$R_{16}$ is H; $CH_3$; $CH_2$-$CH_3$; or $CF_3$; $R_{16}$ being other than H when $R_{15}$ is Cl, $R_a$ is H or $CH_3$, and $R_b$ is H; or IV. R is a radical of formula (d)

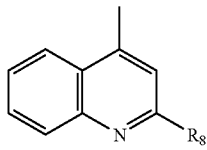

wherein
$R_8$ is 1-piperazinyl, 3-methyl-piperazin-1-yl or 4-benzyl-piperazin-1-yl; or V. R is a radical of formula (e)

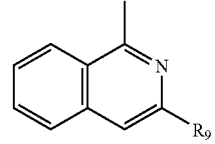

wherein $R_9$ is 4,7-diaza-spiro [2.5] oct-7-yl; or 1-piperazinyl substituted in position 3 by methyl or ethyl and optionally in position 4 by methyl;

or a pharmaceutically acceptable salt thereof.

* * * * *